United States Patent [19]

Wandell

[11] Plant 5,079

[45] Aug. 2, 1983

[54] SUGAR MAPLE TREE NAMED COMMEMORATION

[76] Inventor: Willet N. Wandell, Myra Station Rd., Rte. 3, Box 158, Urbana, Ill. 61801

[21] Appl. No.: 318,616

[22] Filed: Nov. 5, 1981

[51] Int. Cl.[3] ..... A01H 5/00

[52] U.S. Cl. ..... Plt./51

[58] Field of Search ..... Plt./51

*Primary Examiner*—Robert E. Bagwill

*Attorney, Agent, or Firm*—Wm. A. Snow

[57] ABSTRACT

This disclosure concerns a new and distinct variety of *Acer saccharum* (commonly known as sugar maple tree) characterized by its exceptional growth habit with thick, leathery leaves, a tight, compact, oval shaped crown with a heavy distribution of leaves which are not subject to tatter, and its extreme ease of propagation.

3 Drawing Figures

BACKGROUND OF THE INVENTION

This new variety of sugar maple tree was found growing in a planting of sugar maple seedling beds at my Duncan Nursery in rural Champaign, Ill., and grew to a height of five feet in the first year. Each year since, it has had a robust growth habit, better than twice as rapid as usual sugar maple trees, reaching a caliper of six inches (approximately fifteen centimeters) in ten growing seasons. As the tree grew, it exhibited thicker, leathery, darker color leaves with a definite sheen or luster. More leaves appear at the crown than other trees in adjacent rows of sugar maple trees. I now have two hundred trees in my nursery at Urbana, Ill., all propagated by budding.

SUMMARY OF THE INVENTION

A new and distinct cultivar of sugar maple tree characterized by its exceptional growth habit with thick, leathery, dark green leaves with a definite sheen or luster, a tight, compact, moderately spreading crown with a heavy distribution of leaves not subject to leaf tatter as are sugar maples grown in a wide midwest area of the United States, extreme ease of propagation with new bud growth exhibiting tall, straight stems and many well-distributed branches, and the leaves changing to a pronounced shade of red, orange and pink in the Fall, color occurring ten to fourteen days in advance of other sugar maple trees observed, and persisting beyond the first killing frost.

BRIEF DESCRIPTION OF THE DRAWINGS

The other sheet shows the colors of the upper and lower leaf surfaces.

One sheet discloses in the lower photograph leaves from my new variety compared with the leaves of the normal red maple tree on the left. The upper photograph shows the tree taken in the Fall.

The colors shown are as nearly true as it is possible to obtain by conventional photographic procedures.

DETAILED DESCRIPTION OF THE NEW PLANT VARIETY

The following is a detailed description of my new variety of sugar maple tree, the stated observations having been made of trees growing in my nurseries at Champaign and Urbana, Ill., both cities in Champaign County, and in East Central Illinois in general with color designations according to the Horticultural Colour Chart of the British Horticultural Council.

Origin: Seedling.

Parentage and classification: Variant of *Acer saccharum.*

Form: Tree.

Shape: Upright with broad crown.

Height: From 30 feet to 36 feet, growing 5 feet during the first year, including very dense branching. Tree grows with straight trunk and is very robust.

Trunk size: 15 cm. (ten growing seasons).

Growth rate: Relatively fast for the species.

Bark: Medium to dark gray, smooth at first soon becoming shallowly fissured with a tan inner bark revealed in fissures.

Branches: Numerous, stout, glabrous, the lower ones ascending, the upper ones obliquely-upright; first year stems olive-green marked with small, circular lenticels, the second year stems orange-brown and slightly fissured, the third year and older stems brownish-gray.

*Angle of attachment.*—60°.

*Size.*—300 cm. in length and 4 cm. where attached to the bole and 3 mm. at the tip.

*Spacing.*—30–40 cm.

Leaves: Mature.

*Length.*—Up to 15 cm.

*Width.*—20 cm.

*Form.*—Deciduous, opposite, 4-ranked, firm in texture, palmately lobed with 3 large lobes and 2 smaller basal lobes, the bases being subcordate, the lobes long wedge-shaped to their bases and acuminate wedge-shaped, the teeth slightly rounded, the blades of mature leaves broader than long.

*Veins.*—Palmately arranged, reticulate.

*Petioles.*—14 cm. in length.

*Texture.*—Firm and leathery.

*Color.*—131A.

*Pubescence distribution.*—Confined to tufts of hair in the axels of veins on the lower leaf surface.

Winter buds: Sessile, pubescent, narrowly conical olive-brown with 10 to 14, 4-ranked bud scales, the terminal buds 6 to 7 mm. long, the later buds 4-ranked, 3 to 6 mm. long and opposite with good survival rate during the winter months.

Fall color: Vivid red 33A, pink 38A, and orange 168B, with small amount of yellow, the pink and orange colors fade away after a very short space of time.

This variety resembles a sugar maple tree (*Acer saccharum*) and clearly distinguishes from other sugar maple trees by its rapid growth habit in the stand growing under similar field conditions, its darker colored and abundance of leaves with good sheen or luster, holding its distinguishing characteristics through propagation by budding and consistently producing heavily branched, uniform progeny with straight boles, its freedom from leaf tatter, and in the Fall the leaves turning a pronounced shade of red, orange and pink at an early date and persisting.

I claim:

1. A new and distinct variety of sugar maple tree, substantially as herein shown and described, characterized by the unique combination of its relatively fast and dense growth, freedom from leaf tatter, numerous strategically placed branches, its abundance of thick, dark colored, leathery leaves, thick in comparison to most sugar maple trees, with more leaves on the compact oval crown, its relative ease of propagation and an excellent survival rate of buds throughout the winter months, with the leaves turning red, orange and pink in the Fall, the red color exhibiting ten to fourteen days prior to most sugar maple trees with leaves persisting for a longer period of time after the first killing frost than other sugar maple trees observed.

* * * * *

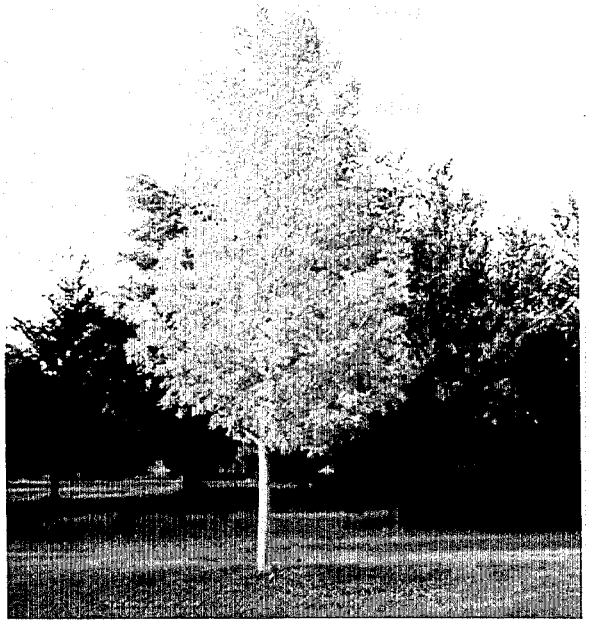
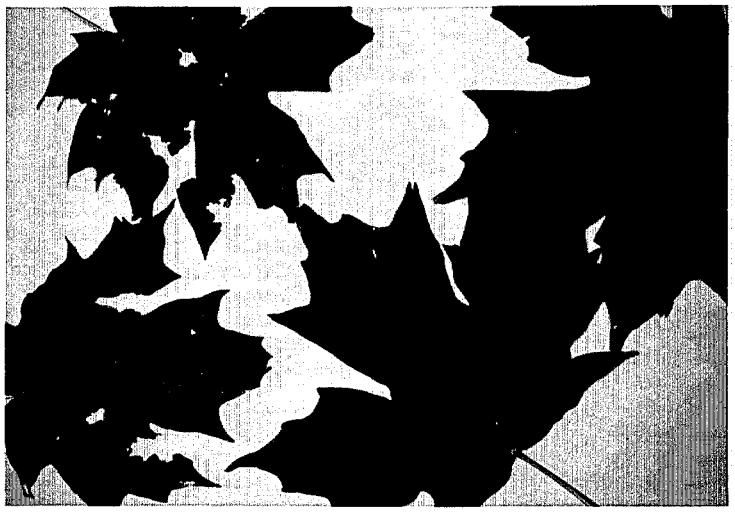

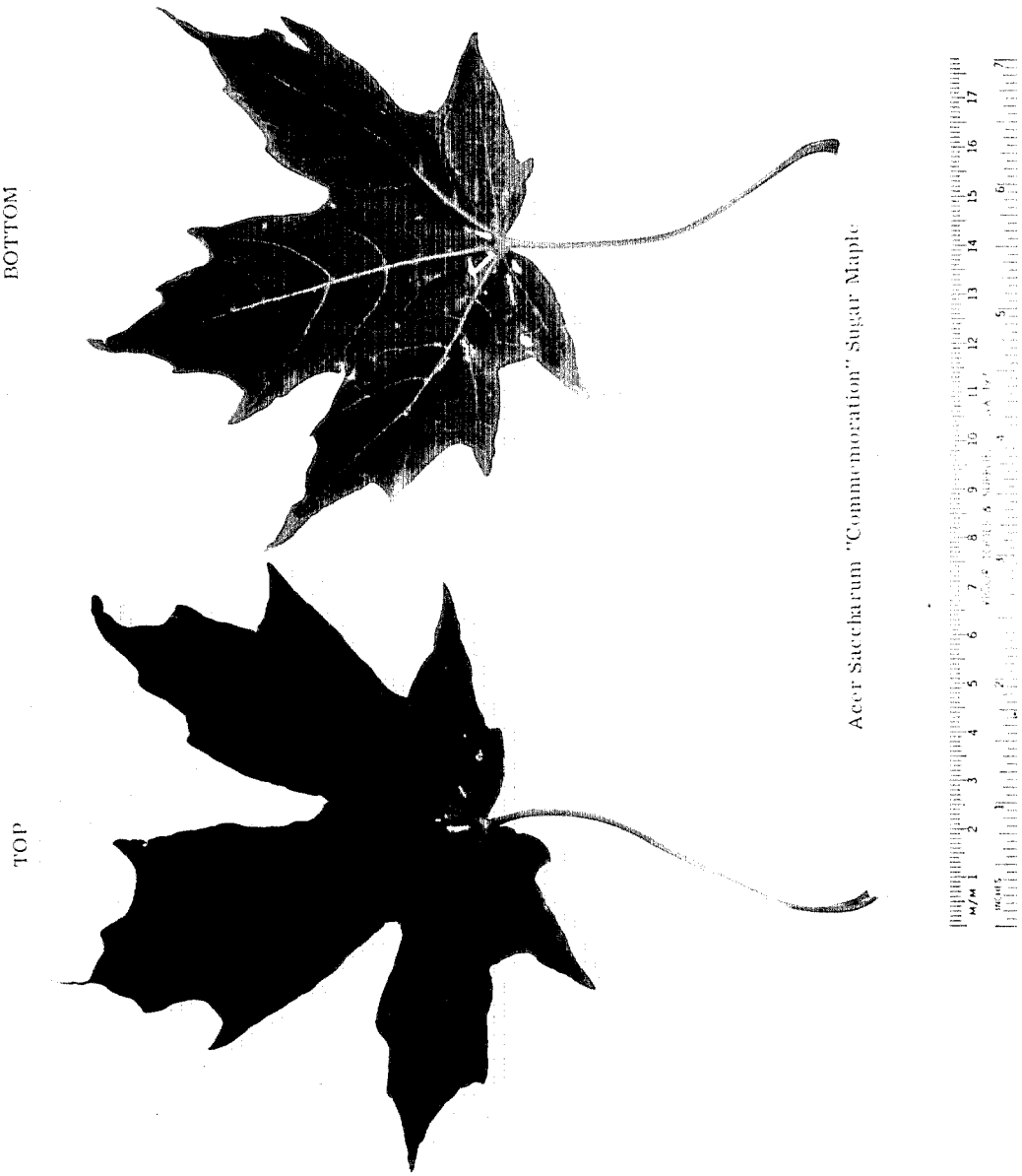
BOTTOM
TOP
Acer Saccharum "Commemoration" Sugar Maple